United States Patent [19]
Wetegrove

[11] Patent Number: 5,796,478
[45] Date of Patent: Aug. 18, 1998

[54] MONITORING OF FILM FORMING LIVING DESPOSITS

[75] Inventor: Robert L. Wetegrove, Winfield, Ill.

[73] Assignee: Nalco Chemical Company, Naperville, Ill.

[21] Appl. No.: 900,546

[22] Filed: Jul. 25, 1997

[51] Int. Cl.$^6$ .................................................. G01N 21/64
[52] U.S. Cl. ...................... 356/318; 250/458.1; 356/244; 356/417
[58] Field of Search .................... 356/38, 244, 317, 356/318, 417; 250/458.1, 459.1, 461.1, 461.2

[56] References Cited

U.S. PATENT DOCUMENTS

| | | | |
|---|---|---|---|
| 4,916,317 | 4/1990 | Gabriel et al. | 356/445 |
| 5,155,555 | 10/1992 | Wetegrove et al. | 356/381 |
| 5,185,533 | 2/1993 | Banks et al. | 356/442 |
| 5,264,917 | 11/1993 | Wetegrove et al. | 356/382 |
| 5,593,850 | 1/1997 | Wetegrove et al. | 435/7.92 |

OTHER PUBLICATIONS

Wilfred H. Nelson article entitled "Modern Techniques For Rapid Microbiological Analysis", pp. 240–257, 1991.

*Primary Examiner*—F. L. Evans
*Attorney, Agent, or Firm*—Hill & Simpson

[57] ABSTRACT

A method and apparatus for detecting, measuring and monitoring films formed on exposed surfaces of a fluid system caused by microorganisms present in the fluid system. Pursuant to the present invention, a fluorometer is utilized to irradiate an exposed surface with light of the appropriate magnitude and intensity which results in an excitation of the NAD(P)H and ATP and other fluorescent molecules contained within microorganisms and subsequent fluorescent emission from the microorganisms. As a result, films caused by the presence of microorganisms in the fluid system can be detected and monitored.

21 Claims, 3 Drawing Sheets

MONITORING OF FILM FORMING LIVING DESPOSITS

BACKGROUND OF THE INVENTION

The present invention relates generally to the monitoring of films on industrial equipment caused by film forming organisms present in industrial water systems. More specifically, the present invention relates to the monitoring and measurement of films caused by living organisms formed on pipe, conduit and vessel surfaces.

The fouling of heat exchange equipment can be caused by living organisms in an industrial water system in addition to the deposits caused by organic and inorganic compounds. Films caused by microorganisms, with or without organic and mineral contents, grow in thickness thereby reducing the efficiency of heat transfer from the hot interior to the cooler exterior or vice versa.

Further, film forming microorganisms are not limited to water systems. Specifically, primitive microorganisms have been found to form films in systems such as natural gas transmission lines.

There are numerous examples of industrial fluid streams where entrain film forming microorganisms reduce the efficiency of the equipment employed in the process. Not only is the efficiency of the equipment reduced, but the microorganisms may contaminate the final product.

One such example is found in papermaking machinery. Bacteria colonies, protozoa and other simple life forms can become entrained in the pulp. The microorganisms can feed and thrive in the pulp slurry and can eventually result in a sticky film on the exposed surfaces of the equipment that can trap other particles in the slurry. Eventually, the papermaking equipment becomes fouled and, due to the turbulence of the slurry, the film becomes part of the paper product, resulting in reduced quality.

The monitoring of films formed on industrial equipment is known but is generally limited to films resulting from the entrainment of organic or inorganic materials in the process fluid. The separate monitoring of films caused by living organisms is not separately provided for. However, the separate monitoring of films caused by living organisms is desirable because microorganisms can often pose unique problems such as product contamination. Further, the presence of microorganisms may result in a product that is not only of a lower quality, but that is unacceptable for sale. Still further, the monitoring of microorganisms may be especially essential in those systems where microorganisms can thrive and multiply due to the presence of acceptable food sources such as a pulp slurry as discussed above with respect to the papermaking industry.

A need, therefore, exists for an improved film monitoring system and film monitoring method that are capable of detecting and monitoring films caused by microorganisms.

SUMMARY OF THE INVENTION

The present invention provides an improved method and apparatus for detecting and monitoring films formed by living organisms entrained in the fluid of a system and further which have a tendency to produce films on surfaces of the system equipment. The apparatus comprises a test surface that is exposed to the fluid of the system and a fluorometer. The fluorometer irradiates the first test surface with a light of a wavelength and intensity sufficient to cause the film forming living organisms that have accumulated on the first test surface to emit fluorescent emissions as a result of the irradiation. The fluorometer further includes a detector for detecting and measuring the intensity of the fluorescent emissions emitted by the film forming living organisms.

In an embodiment, the apparatus comprises a first test surface and a second test surface. The second test surface is maintained in a substantially film-free condition and is used for generating a test or a base signal for comparison with a signal produced by the fluorescent emissions of the first test surface.

In an embodiment, both the first and second test surfaces are disposed on a rotatable disk that is at least partially submerged in the fluid of the system. The disk is rotated so that the first test surface is disposed in front of the fluorometer which irradiates the first test surface and measures the amount and intensity of the fluorescent emissions generated by the film forming organisms disposed on the first test surface. A signal is generated which is proportionate to the amount of film forming organisms disposed on the first test surface.

Then, the disk is rotated so that the second test surface is disposed in front of the fluorometer. To maintain the second test surface in a substantially film-free condition, the second test surface may be comprised of a hydrophobic or hydrophillic material or a coating which inhibits the formation of films thereon. The second test surface can alternatively be cleaned by mechanical, chemical, or hydraulic means. The fluorometer irradiates the second test surface and generates a signal proportionate to the amount of film or microorganisms disposed on the second test surface. This second signal is typically small, and may be zero due to the lack of a substantial film on the second test surface. Then, an analyzer or a controller compares the first signal and the second signal thereby providing an indication of the amount of film disposed on the first test surface.

In an embodiment, the disk is mounted on a shaft which is connected to a motor that rotates the disk. The shaft may be mounted in the center of the disk or away from the center of the disk. That is, the shaft may be mounted in a centric or eccentric manner.

In an embodiment, the disk comprises a variety of test surfaces which simulate different surfaces of the system that are exposed to fluid and on which film forming microorganisms can accumulate.

In an embodiment, especially adapted to processes having a flowing stream of fluid, the apparatus further comprises a transparent shunt conduit for shunting a sample stream of fluid from the main process stream through the shunt conduit. The shunt conduit then includes a first test surface which can be irradiated with a fluorometer.

In an embodiment, the shunt conduit includes a first and a second test surface as well as a first and a second fluorometer. The first fluorometer irradiating the first test surface and detecting and measuring the amount of fluorescence generated by film forming microorganisms that have accumulated on the first test surface. The second fluorometer similarly irradiating the second test surface and detecting and measuring the amount of fluorescence emitted by film forming microorganisms disposed on the second test surface. However, as noted above, the second test surface is maintained in a substantially film-free condition. When the second test surface is disposed in a shunt conduit, the substantially film-free condition may be accomplished by a mechanical wiping apparatus disposed inside the shunt conduit for maintaining the second test surface in a substantially film-free or clean condition. In an embodiment, a section of the shunt conduit may be fabricated from or coated with a hydrophobic material or a material that inhibits the formation of films thereon.

The present invention also provides a method of monitoring the accumulation of film forming organisms on surfaces of an industrial system. The method includes the steps of submerging a first test surface in the fluid of the system, irradiating the first test surface with light of a wavelength and intensity sufficient to cause film forming living organisms that have accumulated on the test surface to emit fluorescent emissions. The method further comprises the step of detecting and measuring the fluorescent emissions emitted by the film forming living organisms as a means for measuring the amount of film that has been deposited on the test surface.

In an embodiment, the method further comprises the step of submerging a second test surface in the fluid of the system, the second test surface being substantially film free. The method further comprising the step of irradiating the second test surface with light of a wavelength and intensity sufficient to cause film forming living organisms that have accumulated on the second test surface to emit fluorescent emissions. The method further comprising the steps of generating a first signal indicative of the intensity of the fluorescence emitted by organisms accumulated on the first test surface and generating a second signal indicative of the intensity of the fluorescence emitted by the organisms accumulated on the second test surface and comparing the first signal with the second signal.

In an embodiment, the first and second test surfaces are disposed in a shunt conduit through which a sample fluid stream passes. The shunt conduit being transparent so that light may be irradiated through the conduit to the first and second test surfaces and so that detectors may be disposed outside of the shunt conduit for detecting fluorescence emitted by organisms disposed on the first and second test surfaces.

In an embodiment, the shunt conduit includes a wiper for removing film accumulations from the second test surface.

In an embodiment, the second test surface is further characterized as being fabricated from hydrophobic material.

In an embodiment, the second test surface is further characterized as being fabricated from a hydrophilic material.

It is therefore an advantage of the present invention to provide an improved apparatus for detecting the formation of films on industrial fluid system surfaces that are caused by film forming microorganisms.

Yet another advantage of the present invention is that it provides an apparatus for distinguishing between films formed by inorganic and non-living organic material from films formed by microorganisms or living material.

Another advantage of the present invention is that it provides an improved method and apparatus for monitoring the formation of films caused by film forming microorganisms.

Additional features and advantages of the present invention are described in, and will be apparent from, the detailed description of the presently preferred embodiments and from the drawings.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

Figures 1, 2:
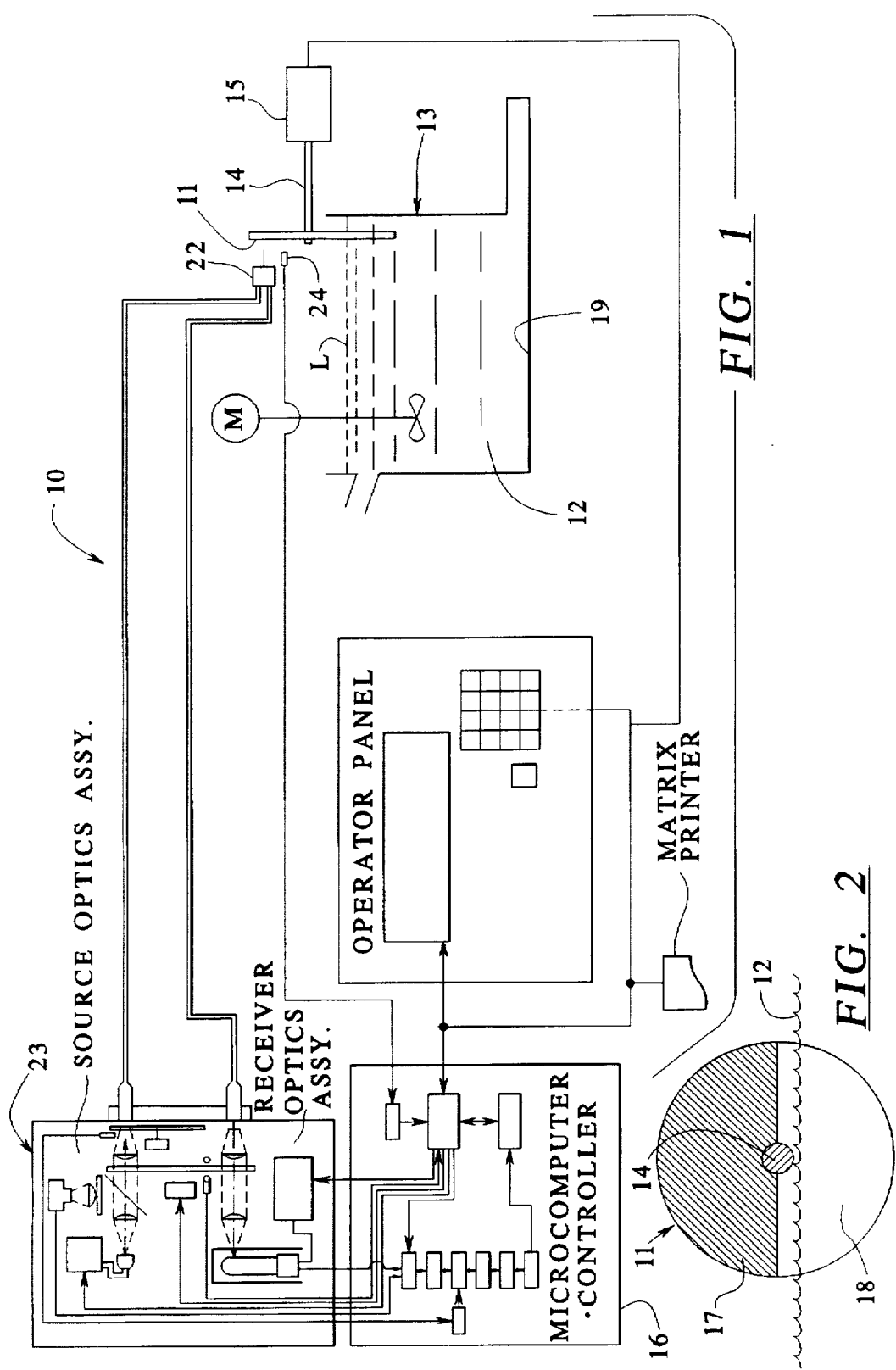
FIG. 1 is a partly diagrammatic, partly schematic illustration of an embodiment of the present invention.
FIG. 2 is a front plan view of a disk used in the embodiment illustrated in FIG. 1.

FIG. 1 illustrates, partly diagrammatically and partly schematically, an apparatus 10 made in accordance with the present invention for determining the formation of a film on a disk 11 that is partially submerged in the fluid 12 of a reservoir 13. The disk 11 is mounted onto a shaft 14 which is connected to a motor 15. The motor periodically rotates the shaft 14 and disk 11 upon receiving a signal from the controller 16.

The disk 11 is further illustrated in FIG. 2. In an embodiment, the disk 11 includes a first surface 17 and a second surface 18. The first surface 17 may be a surface designed to simulate the inside surface 19 of the vessel 13 or another surface of the system which is exposed to the fluid 12. On the other hand, the surface 18 may be a test surface which is designed to inhibit the formation of film on the surface 18. As a result, the test surface 18 serves as a point of reference for determining the amount of film that has subsequently accumulated on the surface 17.

During operation of the apparatus 10, after the test surface 17 has been submerged in the liquid 12 for a period of time, the motor 15 rotates the disk 11 so that the surface 17 is disposed in front of the probe 22 of the fluorometer 23. The fluorometer 23 transmits light radiation through the probe 22 at an intensity and wavelength sufficient to cause the NAD(P)H or ATP or other fluorescent component of film forming microorganisms to become excited and thereafter emit fluorescent radiation. Accordingly, for those films that are formed on the disk 11 by the presence of microorganisms from the fluid 12, radiation transmitted through the probe 22 causes the NAD(P)H and ATP and other fluorescent components to emit fluorescent radiation.

The emitted fluorescent radiation is detected by the detector 24 which sends the signal back to the controller 16. The signal transmitted from the detector 24 to the controller 16 may be compared with another signal generated by irradiating the test surface 18. As discussed above, the test surface 18, in contrast to the test surface 17, may be fabricated from material that is designed to inhibit films from forming on the surface 18. Accordingly, after being radiated with light transmitted by the probe 22, only a minimum amount of fluorescent radiation will be emitted by the surface 18 after it has been rotated in front of the probe 22. The minor amount of fluorescent radiation may be caused by microorganisms suspended in the water which may coat the surface 18. The signal generated as a result of irradiating the test surface 18 serves as a base signal and a point of comparison for the signal generated by irradiating the surface 17. Also, the test surface 18 may be cleaned by mechanical, hydraulic, or chemical means.

In operation, the formation of a film on the surface 17 is periodically monitored by rotating the disk 11 so that the surface 17 is disposed in front of the probe 22. The surface 17 is irradiated by radiation transmitted through the probe 22. Films containing microorganisms are thereafter detected because the microorganisms emit fluorescent radiation due to the presence of NAD(P)H and/or ATP and/or other compounds in the microorganisms. The fluorescent radiation is detected at the detector 24 and a signal is generated by the controller 16 which is proportionate to the amount of fluorescent radiation caused by the film disposed on the surface 17. The disk is then rotated and the procedure is repeated for the test surface 18. The two signals are compared which provides the operator with an indication as to the extent of film formation on the surface 17 which is attributable to the presence of microorganisms in the fluid 12.

Figure 4:
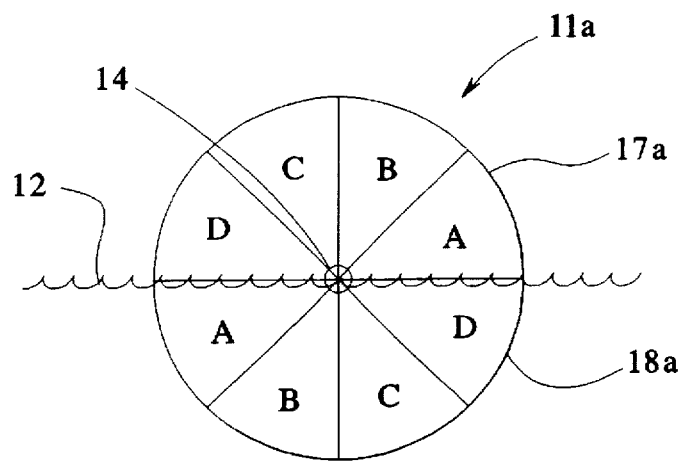
FIG. 4 is a front plan view of a disk used in another embodiment of the present invention.

FIGS. 2, 4, 5 and 6 illustrate representative examples of the disks 11, 11a, 11b and 11c which may be used in connection with the present invention. Specifically, in FIG. 2, a disk 11 is illustrated which is mounted onto a centrically disposed shaft 14. The disk 11 also includes two surfaces 17, 18, one of which (18) is used as a test surface. In FIG. 4, a disk 11a is illustrated which also includes a centrically disposed shaft but where each surface 17a, 18a is divided into four separate subsections A, B, C and D. The different subsections A, B, C and D are intended to simulate the materials of different areas of the water system. Each area A, B, C and D of the surface 17a can be separately examined and compared to the corresponding reference signal generated by the reference area A, B, C and D respectively of the test surface area 18a. It will also be noted that the disk 11a as illustrated in FIG. 4 is in a position where the surface 17a has been rotated in front of the probe 22. Normally, the surface 17a is submerged below the water surface 12.

Figure 5:
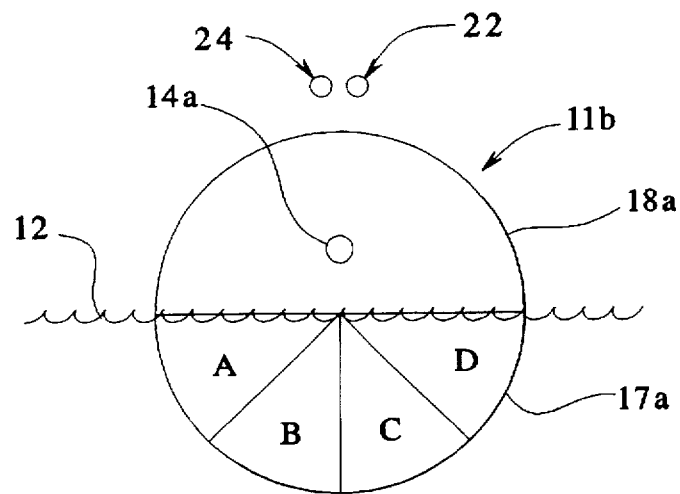
FIG. 5 is a front plan view of a disk used in still another embodiment of the present invention.
Figure 6:
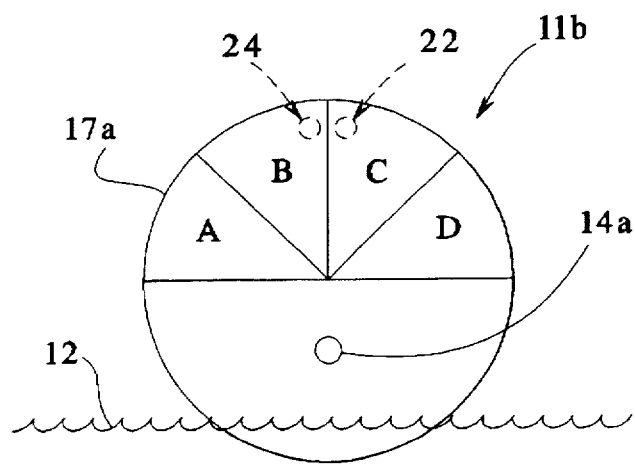
FIG. 6 is a front plan view of the disk shown in FIG. 5 after the surface to be measured has been rotated upward above the surface of the water.

As illustrated in FIGS. 5 and 6, the disk 11b may be mounted onto the shaft 14a in an eccentric manner. If the disk 11a is mounted onto the shaft 14 in a centric manner as shown in FIG. 4, the area to be examined, whether it be the surface 17a or the reference surface 18a, are examined after rotation of the disk 11a. If the disk 11b is mounted eccentrically to the shaft 14a, the readings are compared to a measurement taken without the disk in the light excitation/emission path. Specifically, referring to FIG. 5, the disk 11b has been rotated so that the surface 17a is submerged below the water surface 12. The excitation point 22 and emission measurement point 24 are both disposed above the surface 18a of the disk 11b. In contrast, as shown in FIG. 6, the disk 11b has been rotated so that the excitation point 22 and 24 are disposed behind the surface 17a which has been rotated upward above the surface 12 of the water.

Figure 3:
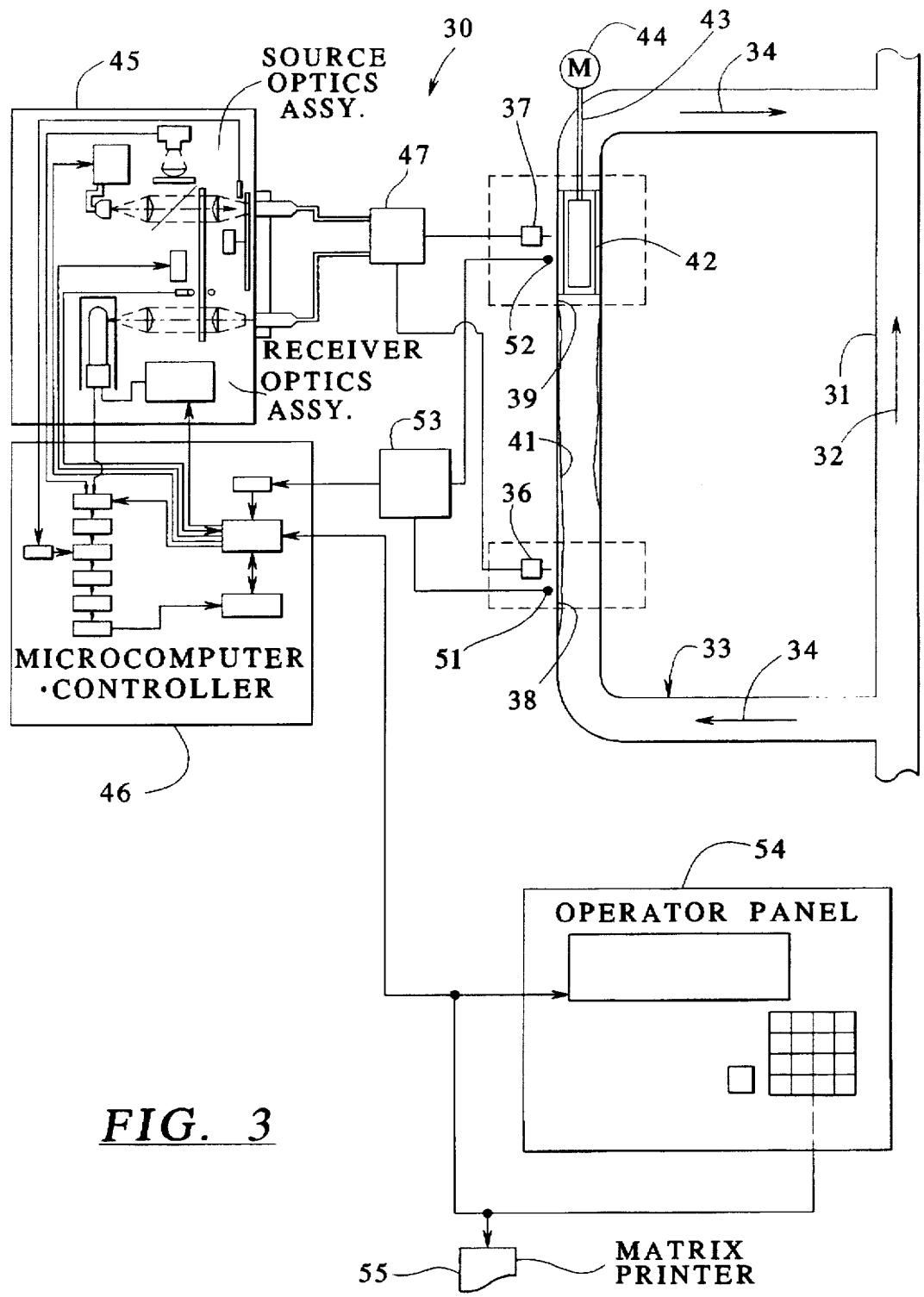
FIG. 3 is a partly diagrammatic, partly schematic illustration of another embodiment of the present invention.

Another embodiment of the present invention is illustrated in FIG. 3. In the apparatus 30 illustrated in FIG. 3, a main conduit 31 of the system being tested includes a stream of process fluid flowing in the direction of the arrows shown at 32. A shunt conduit is shown at 33 which provides a passageway for a sample fluid stream to flow in the direction of the arrows shown at 34. The shunt conduit 33 is preferably transparent so that light radiated by the probes 36, 37 may be easily transmitted through the shunt conduit 33.

In the embodiment illustrated at 30 in FIG. 3, two test surfaces shown at 38, 39 are provided. The test surface shown at 38 is not treated or provided with a special coating in any way and therefore a film shown at 41 eventually begins to form on the surface 38. In contrast, a wiper mechanism shown at 42 is provided in the portion of the shunt conduit in which the surface 39 is disposed. The wiper 42 is connected to a shaft 43 which, in turn, is connected to a motor 44. Periodically, the motor 44 rotates the shaft 43 and wiper 42 thereby cleaning the surface 39 of the shunt conduit 38. The clean surface 39 is then used as a reference surface in a manner similar to the reference surface 18 discussed above with respect to the apparatus 10 illustrated in FIGS. 1 and 2.

In the embodiment illustrated at 30 in FIG. 3, a fluorometer 45 is in communication with both probes 36, 37 through the switch shown at 47. Similarly, the controller 46 is in communication with both detectors 51, 52 through the switch shown at 53. By employing the switches shown at 47, 53, only a single fluorometer 45 and a single controller 46 may be employed. However, separate fluorometers may be employed for the probes 36 and 37 and separate controllers may be employed for the detectors 51, 52.

In operation, radiation is transmitted to the probe 36 through the switch 47 from the fluorometer 45. The radiation is then transmitted through the transparent shunt conduit 33 to the film 41 disposed on the surface 38. In the event the film 41 includes living microorganisms, the NAD(P)H and/or ATP and/or other fluorescent compounds contained in those microorganisms will be excited and will transmit fluorescent radiation which will be detected by the detector shown at 51. A signal from the detector 51 is transmitted through the switch 53 to the controller 46. Subsequently, radiation is transmitted by the fluorometer through the switch 47 and through the probe 37 to the surface 39 which, as noted above, is kept in a clean state by the wiper 42.

The low rate of fluorescent radiation resulting from the coating of fluid disposed on the test surface 39 is detected by the detector 52 and transmitted to the controller 46 by way of the switch 53. Also, the detector 52 may simply detect no fluorescent radiation and a suitable zero signal will be transmitted to the controller 46. Either the controller 46 or a separate controller disposed in the operator panel 54 can then compare the signals generated by the detectors 51, 52 and an estimation of the extent of film formation on the surface 38 can be generated. A printer 55 may be used to present results of the measurement or, in the alternative, a monitor (not shown) may be provided.

It is anticipated that the apparatuses shown at 30 in FIG. 3 and 10 in FIG. 1 may be easily incorporated into existing system which may or may not already be equipped with film forming and monitoring equipment. The apparatuses and methods of the present invention can be used to complement existing film forming and monitoring techniques that are capable of distinguishing between films formed as a result of minerals, inorganic or non-living organic chemicals and films formed as a result of presence of microorganisms in the fluid system.

From the above description, it is apparent that the objects and advantages of the present invention have been achieved. While only certain embodiments have been set forth, alternative embodiments and various modifications will be apparent from the above description to those skilled in the art. These and other alternatives are considered equivalents and within the spirit and scope of the present invention.

What is claimed:

1. An apparatus for detecting and monitoring an amount of film forming living organisms in a system that have a tendency to produce films on equipment surfaces of the system, the apparatus comprising:

a first test surface that is exposed to the fluid of the system, a first fluorometer for irradiating the first test surface with light of a wavelength and intensity sufficient to cause film forming living organisms that have accumulated on the first test surface to emit fluorescent emissions, the first fluorometer further detecting and measuring the fluorescent emissions emitted by the film forming living organisms that have accumulated on the first test surface.

2. The apparatus of claim 1 further comprising a second test surface that is maintained in a substantially film free condition, a second fluorometer for irradiating the second test surface with light of a wavelength and intensity sufficient to cause film forming living organisms that have accumulated on the second test surface to emit fluorescent emissions, the second fluorometer further detecting and measuring the fluorescent emissions emitted by the film forming living organisms that have accumulated on the second test surface.

3. The apparatus of claim 2 wherein the first fluorometer generates a first signal indicative of the intensity of the fluorescence emitted by the organisms accumulated on the first test surface and the second fluorometer generates a second signal indicative of the intensity of the fluorescence emitted by the organisms accumulated on the second test surface, and the apparatus further comprises an analyzer for comparing the first signal and the second signal.

4. The apparatus of claim 1 wherein the first test surface is disposed on a disk that is at least partially submerged in the fluid of the system, the apparatus further comprising a second test surface disposed on the disk, the second test surface being maintained in a substantially film free condition, the first test surface being withdrawn from the fluid prior to being tested for accumulation of organisms by the first fluorometer, the second test surface being withdrawn from the fluid prior to being tested for accumulation of organisms by the first fluorometer.

5. The apparatus of claim 1 wherein the first test surface is disposed on a disk that is at least partially submerged in the fluid of the system, the apparatus further comprising a second test surface dispose on the disk, the second test surface maintained in a substantially film free condition, the first test surface being withdrawn from the fluid prior to being tested for accumulation of organisms by the first fluorometer, the second test surface being withdrawn from the fluid prior to being tested for accumulation of organisms by the first fluorometer, and wherein the first fluorometer generates a first signal indicative of the intensity of the fluorescence emitted by the organisms accumulated on the first test surface and the first fluorometer further generates a second signal indicative of the intensity of the fluorescence emitted by the organisms accumulated on the second test surface, and the apparatus further comprises an analyzer for comparing the first signal and the second signal.

6. The apparatus of claim 1 wherein the first test surface is disposed on a disk that is at least partially submerged in the fluid of the system, the disk accommodating a second test surface, the first test surface being withdrawn from the fluid prior to being tested for accumulation of organisms by the first fluorometer, the second test surface being withdrawn from the fluid prior to being tested for accumulation of organisms by the first fluorometer, the apparatus further comprising a shaft connected to the disk, the shaft connected to a motor, the motor rotating the shaft and the disk so that the first test surface is rotated from submerged position to a position disposed in from of the first fluorometer and back to a submerged position, the motor rotating the shaft and the disk so that the second test surface is rotated from submerged position to a position disposed in from of the first fluorometer and back to a submerged position.

7. The apparat us of claim 1 wherein the system includes a flowing stream of fluid, the apparatus further comprises a transparent shunt conduit for shunting a sample stream from the system, the first test surface being disposed inside the shunt conduit.

8. The apparatus of claim 1 wherein the system includes a flowing stream, the apparatus further comprises a transparent shunt conduit for shunting a sample stream from the system, the first test surface and a second test surface being disposed inside the shunt conduit in a spaced apart relationship, the apparatus further comprising second fluorometer for irradiating the second test surface with light of a wavelength and intensity sufficient to cause film forming living organisms that have accumulated on the second test surface t o em it fluorescent emissions, the second fluorometer further detecting and measuring the fluorescent emissions emitted by the film forming living organisms that have accumulated on the second test surface.

9. The apparatus of claim 8 wherein the shunt conduit includes a wiper for removing film from the second test surface.

10. The apparatus of claim 8 wherein the second test surface is hydrophobic.

11. A method of monitoring the accumulation of film forming organisms on surfaces of an industrial system, the method comprising the following steps:

submerging a first test surface in the fluid of the system, irradiating the first test surface with light of a wavelength and intensity sufficient to cause film forming living organisms that have accumulated on the first test surface to emit fluorescent emissions, detecting and measuring the fluorescent emissions emitted by the film forming living organisms that have accumulated on the first test surface.

12. The method of claim 11 further comprising the steps of submerging a second test surface in the fluid of the system, the second test surface being substantially film free, irradiating the second test surface with light of a wavelength and intensity sufficient to cause film forming living organisms that have accumulated on the second test surface to emit fluorescent emissions, detecting and measuring the fluorescent emissions emitted by the film forming living organisms that have accumulated on the second test surface, generating a first signal indicative of the intensity of the fluorescence emitted by the organisms accumulated on the first test surface, generating a second signal indicative of the intensity of the fluorescence emitted by the organisms accumulated on the second test surface, and comparing the first signal and the second signal.

13. The method of claim 12 wherein the second test surface is hydrophobic.

14. The method of claim 12 wherein the first and second test surfaces are disposed in a shunt conduit through which a sample stream of fluid passes.

15. The method of claim 14 wherein the shunt conduit includes a wiper for removing film from the second test surface.

16. An apparatus for detecting and monitoring an amount of film forming living organisms in a system that have a tendency to produce films on surfaces of the system, the apparatus comprising:

a first test surface that is exposed to the fluid of the system, a first fluorometer for irradiating the first test surface with light of a wavelength and intensity sufficient to cause film forming living organisms that have accumulated on the first test surface to emit fluorescent emissions, the first fluorometer further detecting and measuring the fluorescent emissions emitted by the film forming living organisms that have accumulated on the first test surface, the first fluorometer generating a first signal indicative of the intensity of the fluorescence emitted by the organisms accumulated on the first test surface, the first fluorometer communicating the first signal to a controller, a second test surface that is maintained in a substantially film free condition, a second fluorometer for irradiating the second test surface with light of a wavelength and intensity sufficient to cause film forming living organisms that have accumulated on the second test surface to emit fluorescent emissions, the second fluorometer further detecting and measuring the fluorescent emissions emitted by the film forming living organisms that have accumulated on the second test surface, the second fluorometer generating a second signal indicative of the intensity of the fluorescence emitted by the organisms accumulated on the second test surface, the second fluorometer communicating the second signal to a controller, the controller for comparing the first signal and the second signal and altering conditions within the system if the amount of film accumulated on the first surface exceeds a predetermined limit.

17. The apparatus of claim 16 wherein the system includes a flowing stream, the apparatus further comprises a transparent shunt conduit for shunting a sample stream from the system, the first test surface and a second test surface being disposed inside the shunt conduit in a spaced apart relationship.

18. The apparatus of claim 17 wherein the shunt conduit includes a wiper for maintaining the second test surface in the substantially film free condition.

19. The apparatus of claim 16 wherein the first and second test surfaces are disposed on a rotatable disk that is at least partially submerged in the fluid of the system, the first test surface being disposed on a hydrophilic portion of the disk, the second test surface being disposed on a hydrophobic portion of the disk, the apparatus further comprising a shaft connected to the disk, the shaft being connected to a motor, the motor rotating the shaft and the disk so that the first test surface is rotated from submerged position to a position disposed in from of the first fluorometer and back to a submerged position, the motor rotating the shaft and the disk so that the second test surface is rotated from submerged position to a position disposed in from of the first fluorometer and back to a submerged position.

20. A method of monitoring the accumulation of film forming organisms on surfaces of an industrial system, the method comprising the following steps:

providing a rotating disk with a first test surface and a second test surface, the first test surface being disposed on a hydrophilic portion of the disk, the second test surface being disposed on a hydrophobic portion of the disk, partially submerging the disk in the fluid of the system, rotating the disk so that the first test surface is disposed in front of a fluorometer and so that the second test surface is submerged in the fluid, irradiating the first test surface with light of a wavelength and intensity sufficient to cause film forming living organisms that have accumulated on the first test surface to emit fluorescent emissions, detecting and measuring the fluorescent emissions emitted by the film forming living organisms that have accumulated on the first test surface, generating a first signal indicative of the intensity of the fluorescence emitted by the organisms accumulated on the first test surface, rotating the disk so that the second test surface is disposed in front of the fluorometer and the first test surface is submerged in the fluid, irradiating the second test surface with light of a wavelength and intensity sufficient to cause film forming living organisms that have accumulated on the second test surface to emit fluorescent emissions, detecting and measuring the fluorescent emissions emitted by the film forming living organisms that have accumulated on the second test surface, generating a second signal indicative of the intensity of the fluorescence emitted by the organisms accumulated on the second test surface, and comparing the first signal and the second signal.

21. A method of monitoring the accumulation of film forming organisms on surfaces of an industrial system, the method comprising the following steps:

providing a shunt conduit for permitting a sample flow of fluid from the system, the shunt conduit comprising a first test surface and a second test surface, the shunt conduit comprising a wiper for wiping the second test surface and maintaining the second test surface in a substantially film free condition, irradiating the first test surface with light of a wavelength and intensity sufficient to cause film forming living organisms that have accumulated on the first test surface to emit fluorescent emissions, detecting and measuring the fluorescent emissions emitted by the film forming living organisms that have accumulated on the first test surface, generating a first signal indicative of the intensity of the fluorescence emitted by the organisms accumulated on the first test surface, irradiating the second test surface with light of a wavelength and intensity sufficient to cause film forming living organisms that have accumulated on the second test surface to emit fluorescent emissions, detecting and measuring the fluorescent emissions emitted by the film forming living organisms that have accumulated on the second test surface, generating a second signal indicative of the intensity of the fluorescence emitted by the organisms accumulated on the second test surface, and comparing the first signal and the second signal.

* * * * *